(12) United States Patent
Applegate et al.

(10) Patent No.: US 7,264,709 B2
(45) Date of Patent: Sep. 4, 2007

(54) METHOD AND APPARATUS FOR CONDITIONING A SENSOR FOR MEASURING OXIDATION REDUCTION POTENTIAL

(75) Inventors: Charles S. Applegate, Brookfield, WI (US); David W. Dubey, Mukwonago, WI (US)

(73) Assignee: Siemens Water Technologies Holding Corp., Warrendale, PA (US)

( * ) Notice: Subject to any disclaimer, the term of this patent is extended or adjusted under 35 U.S.C. 154(b) by 240 days.

(21) Appl. No.: 10/946,512

(22) Filed: Sep. 21, 2004

(65) Prior Publication Data

US 2006/0060475 A1 Mar. 23, 2006

(51) Int. Cl.
*G01N 27/38* (2006.01)
(52) U.S. Cl. .................. 205/775; 205/792; 204/402
(58) Field of Classification Search ................ 204/402, 204/434; 205/775, 792, 794.5
See application file for complete search history.

(56) References Cited

U.S. PATENT DOCUMENTS

| | | | |
|---|---|---|---|
| 4,772,375 A | 9/1988 | Wullschleger et al. | |
| 5,106,478 A * | 4/1992 | Musow et al. | 204/402 |
| 5,210,496 A * | 5/1993 | Hafner | 324/439 |
| 5,470,484 A | 11/1995 | McNeel | |
| 6,096,275 A * | 8/2000 | Greenberg | 422/82.02 |
| 6,579,440 B2 | 6/2003 | Connelly et al. | |
| 6,623,647 B2 | 9/2003 | Martin | |
| 6,758,960 B1 * | 7/2004 | Robertson | 205/775 |

FOREIGN PATENT DOCUMENTS

JP  2000-88801 A * 3/2000

OTHER PUBLICATIONS

Certified translation of JP 2000-88801, Mar. 31, 2000.*

* cited by examiner

*Primary Examiner*—Kaj K. Olsen

(57) ABSTRACT

A method and apparatus for conditioning a sensor to measure an oxidation reduction potential of an aqueous solution such that the time to obtain a reliable oxidation reduction potential measurement is substantially reduced. Such conditioning is often necessary when the sensor is moved from potentiometric equilibrium (e.g., the sensor is cleaned, the sensor is exposed to air, and the like). The method may comprise generating a current through a measurement electrode and a reference electrode of the sensor for a duration of time. A reliable oxidation reduction potential measurement can be made as the voltage across the measurement electrode and the reference electrode stabilizes after the duration of time. Depending on the aqueous solution, the stabilized value can be constant or variable.

22 Claims, 4 Drawing Sheets

PRIOR ART

METHOD AND APPARATUS FOR CONDITIONING A SENSOR FOR MEASURING OXIDATION REDUCTION POTENTIAL

FIELD OF THE INVENTION

The invention relates to measuring oxidation reduction potential of an aqueous solution.

BACKGROUND OF THE INVENTION

Oxidation reduction potential (ORP) is a measure of the capacity of an aqueous solution to either release electrons in chemical reactions (i.e., oxidation) or gain electrons in chemical reactions (i.e., reduction). Oxidation and reduction reactions control the behavior of many chemical constituents in aqueous solutions of drinking water, wastewater, and aquatic environments.

SUMMARY OF THE INVENTION

In one embodiment, the invention may provide a method of conditioning a sensor for measurement of an oxidation reduction potential of an aqueous solution. The sensor can include a measurement electrode, a reference electrode, and a voltmeter to measure a voltage across the measurement electrode and the reference electrode. The method may comprise placing the measurement electrode and the reference electrode in the aqueous solution, generating a current through the measurement electrode and the reference electrode by applying a voltage to at least one of the measurement electrode and the reference electrode for a duration of time, and measuring an oxidation reduction potential of the aqueous solution after the duration of time.

In another embodiment, the invention may provide a method of conditioning a sensor for measurement of an oxidation reduction potential of an aqueous solution. The sensor can include a measurement electrode, a reference electrode, and a voltmeter to measure a voltage across the measurement electrode and the reference electrode. The method may comprise generating a current through the measurement electrode and the reference electrode by applying a voltage to at least one of the measurement electrode and the reference electrode for a duration of time.

In yet another embodiment, the invention may provide a sensor assembly for measuring an oxidation reduction potential of an aqueous solution. The assembly may comprise a measurement electrode, a reference electrode, a voltmeter, and a current source. The voltmeter can be configured to measure a voltage across the measurement electrode and the reference electrode. The current source can be configured to generate a current through the measurement electrode and the reference electrode by applying a voltage to at least one of the measurement electrode and the reference electrode.

In still another embodiment, the invention may provide a sensor assembly for measuring an oxidation reduction potential of an aqueous solution. The assembly may comprise a measurement electrode, a reference electrode, a voltmeter, and a voltage source. The voltmeter can be configured to measure a voltage across the measurement electrode and the reference electrode. The voltage source can be configured to generate a current through the measurement electrode and the reference electrode by applying a voltage to at least one of the measurement electrode and the reference electrode.

Further aspects of the invention, together with the organization and manner of operation thereof, will become apparent from the following detailed description of the invention when taken in conjunction with the accompanying drawings wherein like elements have like numerals throughout the drawings.

BRIEF DESCRIPTION OF THE DRAWINGS

The invention is further described with reference to the accompanying drawings, which show constructions of the invention. However, it should be noted that the invention as disclosed in the accompanying drawings is illustrated by way of example only. The various elements and combinations of elements described below and illustrated in the drawings can be arranged and organized differently to result in constructions which are still within the spirit and scope of the invention. Also, it is understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" are used broadly and encompass both direct and indirect mountings, connections, supports, and couplings. Further, "connected" and "coupled" are not restricted to physical or mechanical connections or couplings.

DETAILED DESCRIPTION

Oxidation reduction potential (ORP) is a measure of the capacity of an aqueous solution to either release electrons in chemical reactions (i.e., oxidation) or gain electrons in chemical reactions (i.e., reduction). Numerous instruments such as ORP sensors are available to measure the ORP of aqueous solutions. By taking accurate measurements of ORP, the state of various aqueous environments can be determined. Accordingly, the environments can be appropriately modified. For example, ORP measurements in a wastewater treatment system can be used to determine whether the environment requires more or less oxygen or DO. The significance of ORP is well-known in the art. For more background on oxidation and reduction reactions mediating the behavior of many chemical constituents in wastewater, see *Oxidation-Reduction Potential (ORP) method* 2580, Standard Methods for the Examination of Water and Wastewater, $20^{th}$ Edition, Published by American Public Health Association, American Water Works Association, and Water Environment Federation (1998), which is hereby fully incorporated by reference.

Generally, ORP sensors include an inert metal measurement electrode, a reference electrode, and a voltmeter that measures the voltage across the measurement electrode and the reference electrode. This voltage is representative of the ORP of the aqueous solution in which the measurement electrode and the reference electrode are positioned. ORP sensors generally work efficiently when measuring ORP of an oxidizing aqueous solution (e.g., measuring the oxidizing ability of chlorine in swimming pools). However, the conditioning time to obtain a reliable reading can be extremely long when using an ORP sensor to measure ORP of a reducing aqueous solution. Further, because such conditioning is generally required each time the measurement electrode and/or the reference electrode of the ORP sensor is removed from potentiometric equilibrium (e.g., the measurement electrode and/or the reference electrode is cleaned, exposed to air, and the like), such delays can affect processes that depend upon ORP measurements.

Accordingly, the invention provides methods and apparatus for conditioning a sensor for measurement of ORP of an aqueous solution, such that the time to establish a reliable reading is significantly reduced. In some embodiments, the invention is utilized to condition a sensor for measurement of ORP of a mildly reducing aqueous solution as found in biological nutrient removal (BNR) wastewater treatment processes.

Figure 1:
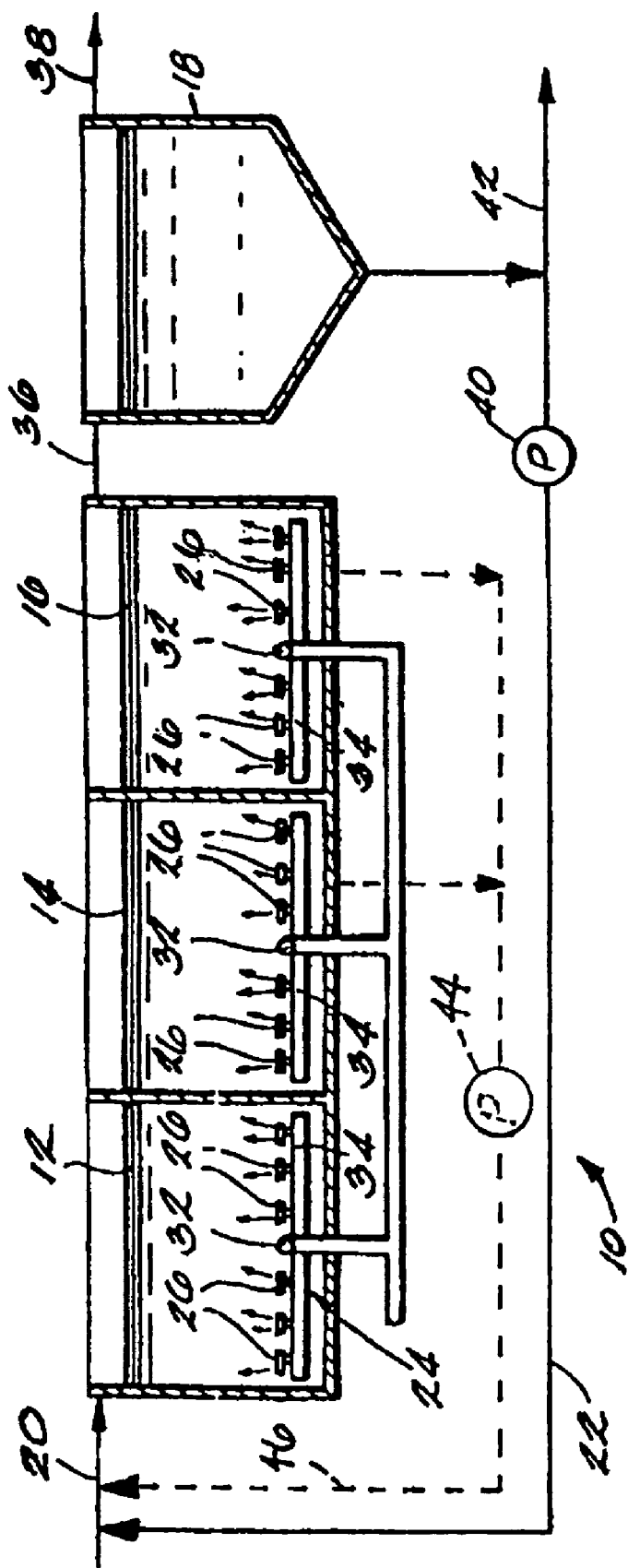
FIG. 1 is a schematic representation of an activated sludge wastewater treatment system for practicing biological nutrient removal wastewater treatment processes.

FIG. 1 schematically illustrates one example of a wastewater treatment system 10 for practicing a BNR wastewater treatment process. The system 10 includes a first aeration zone or tank 12, a second aeration zone or tank 14, a third aeration zone or tank 16, and a settling tank or clarifier 18. A wastewater influent is introduced into the first aeration tank 12 via a conduit 20. The wastewater generally contains a combination of organic compounds, nitrogen compounds, and/or phosphorous compounds. The wastewater may be subjected to screening and/or a preliminary sedimentation treatment to remove large particulate materials prior to introduction into the first aeration tank 12. An activated sludge is introduced into the first aeration tank 12 via a conduit 22. A majority of the activated sludge is recycled from the clarifier 18. The wastewater and the recycled activated sludge are mixed (e.g., homogeneously) in the first aeration tank 12 to form a mixed liquor. Generally, the wastewater and the activated sludge are mixed by air bubbles generated when an oxygen-containing gas (e.g., air) is introduced into the first aeration tank 12 via an aeration device 24.

The illustrated aeration devices 24 include a plurality of conventional diffusers 26 mounted to conduits 34 in a grid-like array. Oxygen-containing gas may be supplied to the diffusers 26 via the conduits 34 under pressure through a manifold 32. The oxygen-containing gas flows through a plurality of perforations in a membrane of the diffuser 26 to from a plurality of air bubbles. Air bubbles rising from the diffusers 26 serve the dual functions of providing the necessary mixing action for the mixed liquor and establishing a supply of oxygen that is less than or equal to the biological oxygen demand of the mixed liquor. In some processes, mechanical mixing and/or mechanical aerators may be utilized to supplement or replace the mixing provided by the aeration devices 24.

The mixed liquor flows by gravity from the first aeration tank 12 to the second aeration tank 14, and from the second aeration tank 14 to the third aeration tank 16. The environmental conditions of each of the first, second, and third aeration tanks 12, 14, and 16 can be controlled to optimize the efficiency and the reliability of the overall wastewater treatment process. The mixed liquor is transferred from the third aeration tank 16 through a conduit 36 into the clarifier 18. The activated sludge settles in the clarifier 18 and a clarified effluent or supernatant is withdrawn from the upper portion of the clarifier via a conduit 38 for further treatment prior to disposal or reuse. A portion of the settled activated sludge withdrawn from the bottom portion of the clarifier 18 is recycled by a pump 40 through the conduit 22 back to the first aeration tank 12 as illustrated in FIG. 1. Another portion of the settled activated sludge is removed via a conduit 42. In some embodiments, enhanced BNR may be obtained by recycling a portion of the mixed liquor from at least one of the first aeration tank 12, the second aeration tank 14, the third aeration tank 16, and a combination thereof to an aeration tank 12, 14, and 16 other than the next aeration tank in the BNR wastewater treatment process sequence. For example, with reference to the pump 44 and the conduit 46 shown in dotted lines in FIG. 1, a portion of the mixed liquor of the second aeration tank 14 and/or the third aeration tank 16 may be recycled by the pump 44 through the conduit 46 to the first aeration tank 12.

The first, second, and third aeration tanks 12, 14 and 16, can be a single tank or basin divided into three separate zones by partitions or walls as illustrated in FIG. 1, or can be completely separate tanks or basins connected by suitable conduit means. The illustrated wastewater treatment process represents a continuous wastewater treatment process. In other embodiments, the wastewater treatment process represents a batch wastewater treatment process. It should be understood that the wastewater treatment system 10 is merely shown and described as an example of a source of an aqueous solution in which the ORP can be measured using the methods and apparatus of the invention. In other embodiments, the methods and apparatus of the invention can be utilized to measure ORP in other aqueous solutions (e.g., oxidizing aqueous solutions).

Figure 5:
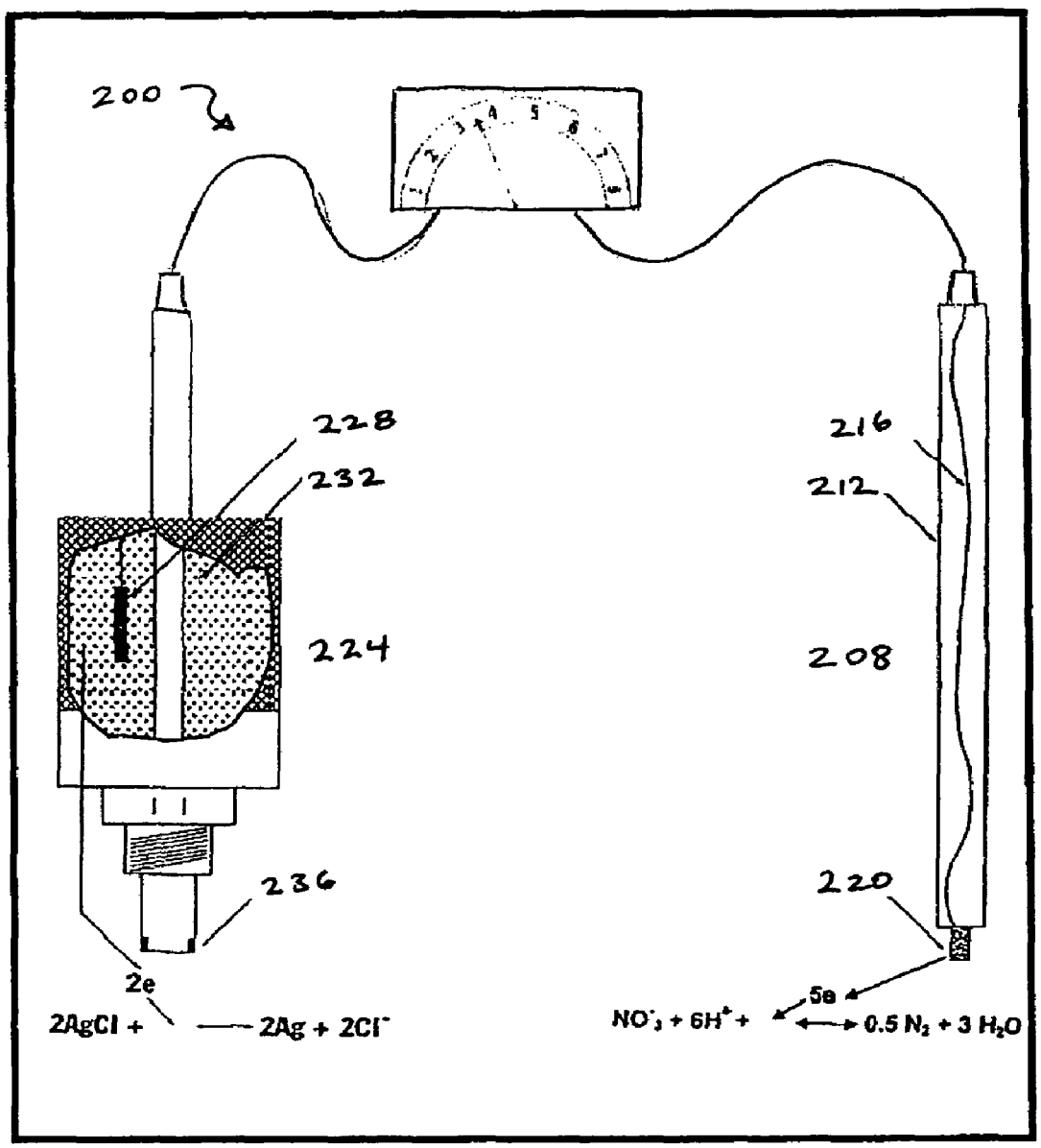
FIG. 5 is a schematic representation of a sensor assembly for practicing the invention.

FIG. 5 illustrates an alternative sensor assembly 200. The assembly 200 includes a sensing cell 208, which acts as a conduit of electrons to a nitrate reduction reaction. The cell has a glass tube 212, a connecting wire 216 and a platinum element 220. The sensing half-cell reaction is shown in FIG. 5. The assembly 200 also includes a reference cell 224, which provides a stable half-cell voltage against which the sensing cell voltage is compared. The reference cell 228 may include a silver-silver chloride element 228, a potassium chloride-silver chloride reference solution 232, and a liquid junction 236. The reference half-cell reaction is shown in FIG. 5.

Figure 2:
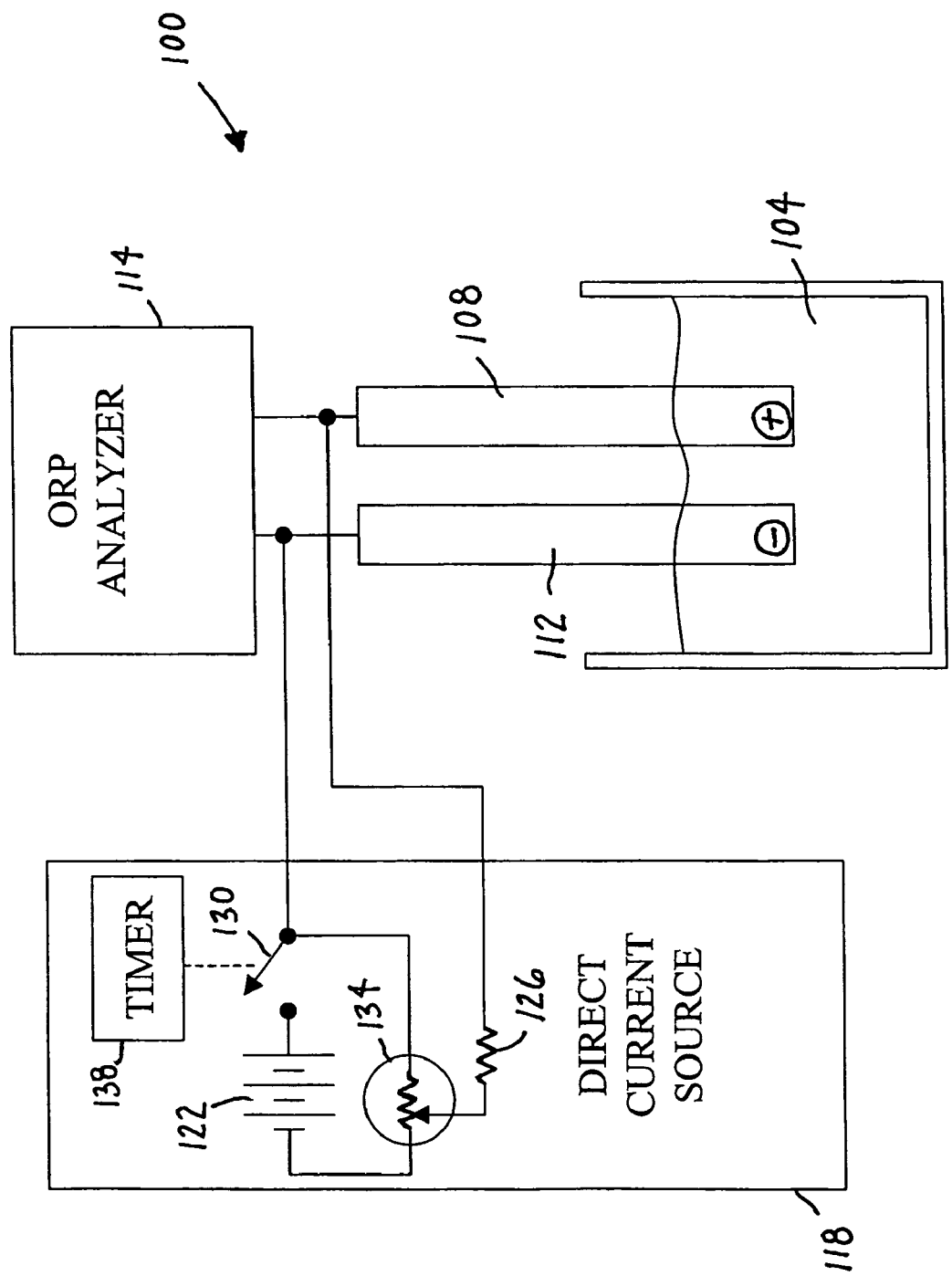
FIG. 2 is a schematic representation of a sensor assembly for practicing the invention.

FIG. 2 illustrates a sensor assembly 100 for measuring ORP of an aqueous solution 104. The sensor assembly 100 includes a measurement electrode 108 (e.g., an inert noble metal electrode such as a platinum electrode, a gold electrode, and the like), a reference electrode 112, an ORP analyzer 114, and a current source 118. It should be understood that the sensor assembly 100 is schematically illustrated and that the construction of the sensor assembly 100 can vary. For example, in some embodiments, the entire sensor assembly 100 can be incorporated into a single unit. In other embodiments, the sensor assembly 100 can comprise a plurality of units. In other embodiments, for example, the sensor assembly 100 can include Strantrol Model No. 880 ORP Controller and Sensor manufacturer by U.S. Filter's Stranco Products. Also, it should be understood that the sensor assembly 100, in some embodiments, can include a voltage source (not shown) in lieu of the current source 118.

The illustrated ORP analyzer 114 includes a voltmeter configured to measure a voltage across the measurement electrode 108 and the reference electrode 112. The voltage across the measurement electrode 108 and the reference electrode 112 is representative of the ORP of the aqueous solution 104 in which the measurement electrode 108 and the reference electrode 112 are positioned. The circuitry of the ORP analyzer 114 can vary greatly depending on the features of the associated ORP sensor.

The illustrated current source 118 includes a voltage source 122 (e.g., a battery, particularly, two AA batteries), a current limit resistor 126, a switch 130, a potentiometer 134, and a timer 138. In other embodiments, the current source 118 can be alternatively constructed. In some embodiments, a voltage source, such as, for example, the voltage source 122, can be included in the sensor assembly 100 in replace of the current source 118. When the measurement electrode 108 and the reference electrode 112 are placed in the aqueous solution 104, the switch 130 can be closed to electrically couple the current source 118 to the measurement electrode 108 and the reference electrode 112. Such electrical coupling allows the current source 118 to apply a voltage to at least one of the measurement electrode 108 and the reference electrode 112. Application of the voltage generates a current through the measurement electrode 108 and the reference electrode 112. Although the circuitry does not form a complete loop for current flow, the ions in the aqueous solution 104 act to complete the loop for current flow.

The current generated through the measurement electrode 108 and the reference electrode 112 can be controlled by controlling the voltage applied, the duration of time the voltage is applied, and/or the duration of time the current is generated. In the illustrated embodiment, the amperage of the current depends on the portion of the voltage source 122 selected using the potentiometer 134 and the impedance of the current limiting resistor 126. The illustrated voltage source 122 comprises a 1.5 volt battery, the illustrated potentiometer 134 comprises a 1 megaohm resistor, and the illustrated current limiting resistor 126 comprises a 500 ohm resistor. Accordingly, the current source 118 can generate a current having an amperage between about 0 mA and about 3 mA. In other embodiments, the level of amperage can vary. However, the level of amperage generally should not exceed a level that would damage the measurement electrode 108, the reference electrode 112, and/or the ORP analyzer 114. Further, although the voltage source 122 is illustrated as a battery having its polarity orientated in a particular direction, in other constructions other types, such as cyclic voltage sources, and/or oppositely orientated voltage sources can be utilized.

In other embodiments, the current source 118 can be configured to provide a current of a first polarity (e.g., a positive polarity) as well as a current of a second polarity (e.g., a negative polarity). For example, in one embodiment (not shown), the current source 118 can include a first voltage source 122, such as a battery, orientated in a first direction and generating a current in a first direction. In this embodiment, the current source 118 can also include a second voltage source 122, such as another battery, orientated in an opposite direction and generating a current in the opposite direction, compared to the first voltage source 122. In further embodiments, the sensor assembly 100 can include more current sources 118 and/or more voltage sources 122 than shown and described.

As the voltage is applied, a voltage associated with the generated current can be measured across the measurement electrode 108 and the reference electrode 112. This voltage generally inversely varies with the level of amperage of the generated current.

In the illustrated embodiment, the duration of time the voltage is applied is controlled by the switch 130. When the switch 130 is closed, a current is generated. When the switch 130 is open, a current is not generated. In the illustrated embodiment, the timer 138 is utilized to trigger closing and opening of the switch 130. In some embodiments, the timer 138 can communicate with circuitry of the ORP analyzer 114 to close the switch 130 when certain conditions exist (e.g., completion of a cleaning process, decay of the ORP measurements after a spike in ORP measurements due to exposure of the measurement electrode 108 and/or the reference electrode 112 to the air, and the like). In other embodiments, an operator can manually actuate the timer 138 to close the switch 130. The timer 138 can be set to open the switch 130 after a duration of time expires. In other embodiments, the switch can comprise a manual switch. In yet other embodiments, other means can be utilized to electrically couple the current source 118 to the measurement electrode 108 and the reference electrode 112.

Figure 3:
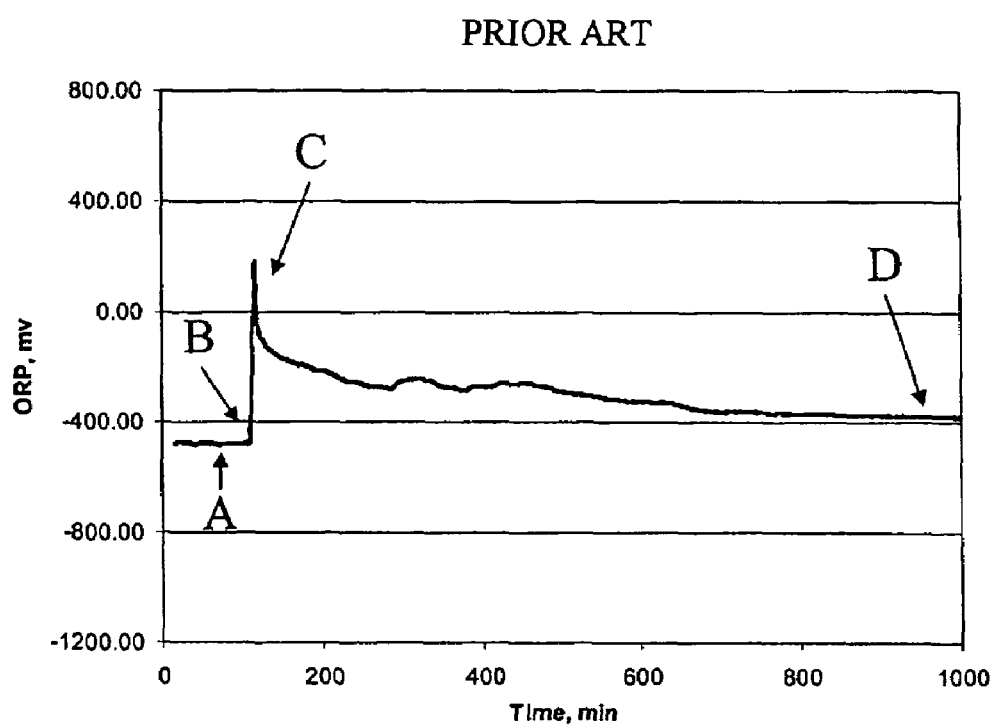
FIG. 3 is a plot of oxidation reduction potential measurements obtained using a prior art sensor assembly.
Figure 4:
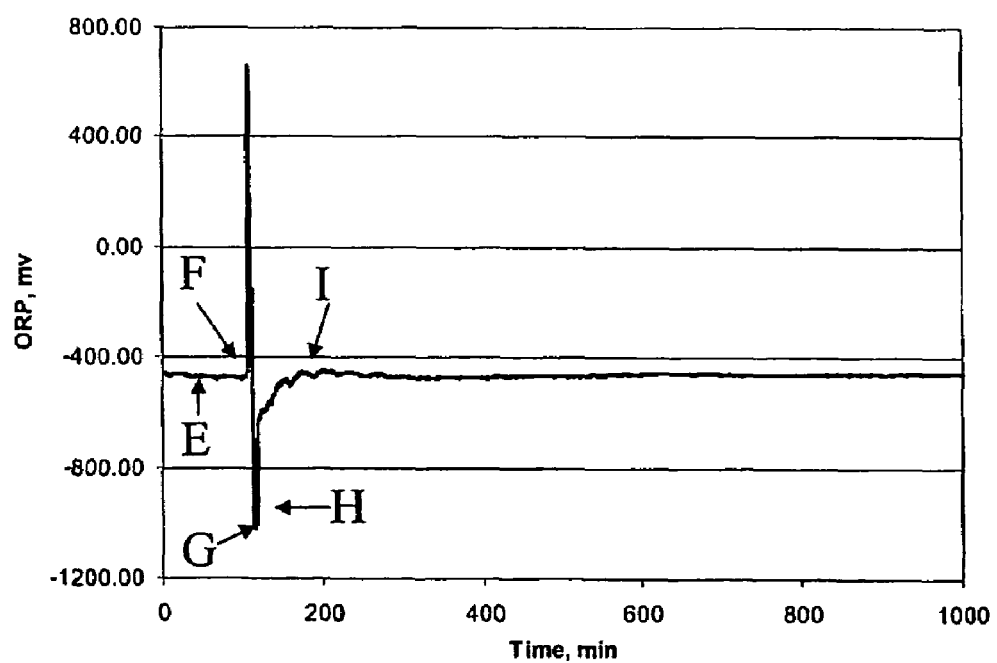
FIG. 4 is a plot of oxidation reduction potential measurements obtained using the sensor assembly of FIG. 2.

Generation of a current through the measurement electrode 108 and the reference electrode 112 using the current source 118 (or voltage source) can greatly reduce the time that it takes to achieve reliable ORP measurements. FIGS. 3 and 4 illustrate that use of the invention can greatly reduce the time required to achieve a stable, reliable ORP measurement from over 1000 minutes (FIG. 3) to approximately 60 minutes (FIG. 4) when compared with prior art measurement techniques. In further construction, the invention can reduce the time required to achieve reliable ORP measurements in less than 60 minutes. The ORP measurement plots illustrated in FIGS. 3 and 4 were obtained from an aqueous solution having an ORP of approximately −470 mV.

With reference to FIG. 3, which illustrates ORP measurements obtained using prior art measurement techniques, at reference A, the ORP measurements have reached potentiometric equilibrium, therefore, the ORP measurements accurately represent the ORP of the aqueous solution. At reference B, the measurement electrode 108 and the reference electrode 112 are exposed to air or another aqueous solution (e.g., a cleaner or cleaning process) causing the ORP measurement to move from potentiometric equilibrium and spike. In other embodiments, at reference B, at least one of the measurement electrode 108 and the reference electrode 112 are removed from the aqueous solution 104. At reference C, the measurement electrode 108 and/or the reference electrode 112 are returned to the aqueous solution 104. The ORP measurements then decay toward the −470 mV ORP value of the aqueous solution 104. As illustrated at reference D, after approximately 1000 minutes, the ORP measurement is still approximately 100 mV above the −470 mV ORP value. As discussed above, such delay can affect processes that depend on ORP measurements.

With reference to FIG. 4, which illustrates ORP measurements obtained using measurement techniques according to the invention, references E and F correspond to references A and B of FIG. 3. However, instead of simply returning the measurement electrode 108 and the reference electrode 112 to the aqueous solution 104 and allowing the ORP measurements to slowly decay toward a reliable value, a voltage is applied at reference G to at least one of the measurement electrode 108 and the reference electrode 112 for a duration of time (e.g., 5 minutes) such that a current is generated through the measurement electrode 108 and the reference electrode 112. In the illustrated embodiment, the voltage is applied to the electrodes 108 and 112 when the electrodes 108 and 112 are at least partially submerged in the aqueous solution.

In some embodiments, the current source 118 can generate a current through the measurement electrode 108 having the same polarity as the aqueous solution 104. For example, in the illustrated embodiments of FIGS. 2 and 4, the current source 118 can provide a voltage having a negative polarity to the electrodes 108 and 112 when the assembly 100 is obtaining ORP measurements for a reducing aqueous environment, such as the aqueous environment 104 graphically represented in FIG. 4. In some embodiments, such as the embodiment illustrated in FIG. 4, the application of a voltage (e.g., a negative current in the illustrated embodiment) causes the electrical potential of the measurement electrode 108 to exceed the measurement solution ORP. As shown in FIG. 4, for example, this produces a faster conditioning time for the measurement electrode 108.

In other embodiments, for example, the current source 118 can generate a current having a positive polarity to the electrodes 108 and 112 when the assembly 100 is obtaining ORP measurements for an oxidizing aqueous environment. In further embodiments, the current source 118 can generate an alternating current or a modulated current.

In the illustrated embodiment of FIG. 4, a current voltage associated with the generated current can be approximately −1000 mV, which is more negative than the −470 mV ORP value of the aqueous solution 104. In other embodiments, the resulting current, the duration of time, and/or the voltage associated with the resulting current can vary. For example, in some embodiments, the voltage applied to the electrodes 108 and 112 can result in a substantially constant direct current (e.g., approximately 0.1 mA), an alternating current, or a variable or modulated current, such as, a ramped current, a stepwise current, an exponentially-increasing current, an exponentially-decreasing current, a triangular current, a combination thereof or the like.

Still referring to FIG. 4, the voltage is removed at reference H and the ORP measurements move toward the −470 mV ORP value of the aqueous solution 104. As illustrated at reference I, after approximately 60 minutes, the ORP measurements have returned to the expected 470 mV ORP value, thus returning to potentiometric equilibrium.

The embodiments described above and illustrated in the figures are presented by way of example only and are not intended as a limitation upon the concepts and principles of the invention. As such, it will be appreciated by one having ordinary skill in the art that various changes in the elements and their configuration and arrangement are possible without departing from the spirit and scope of the invention as set forth in the appended claims. The claimed steps in the claimed methods need not be performed in the order listed, unless specifically stated so.

What is claimed is:

1. A method of conditioning a sensor for measurement of an oxidation reduction potential of an aqueous solution, the sensor having a measurement electrode, a reference electrode, and a voltmeter to measure a voltage across the measurement electrode and the reference electrode, the method comprising:
    placing the measurement electrode and the reference electrode in the aqueous solution;
    removing at least one of the measurement electrode and the reference electrode from the aqueous solution;
    placing the at least one of the measurement electrode and the reference electrode back in the aqueous solution;
    generating a current through the measurement electrode and the reference electrode by applying a voltage to at least one of the measurement electrode and the reference electrode for a duration of time substantially immediately after placing the at least one of the measurement electrode and the reference electrode back in the aqueous solution; and
    measuring an oxidation reduction potential of the aqueous solution after the duration of time.

2. A method according to claim 1, and further comprising allowing a voltage across the measurement electrode and the reference electrode to establish a reliable reading prior to measuring a reliable oxidation reduction potential of the aqueous solution.

3. A method according to claim 1, wherein the aqueous solution comprises a reducing aqueous solution.

4. A method according to claim 1, wherein the aqueous solution comprises an aqueous solution of a wastewater treatment process.

5. A method according to claim 1, wherein generating a current through the measurement electrode and the reference electrode comprises generating a substantially constant direct current through the measurement electrode and the reference electrode.

6. A method according to claim 1, wherein generating a current through the measurement electrode and the reference electrode comprises generating a variable current through the measurement electrode and the reference electrode.

7. A method according to claim 1, and further comprising exposing at least one of the measurement electrode and the reference electrode to air prior to placing the at least one of the measurement electrode and the reference electrode back in the aqueous solution.

8. A method according to claim 1, and further comprising cleaning at least one of the measurement electrode and the reference electrode prior to placing the at least one of the measurement electrode and the reference electrode back in the aqueous solution.

9. A method of conditioning a sensor for measurement of an oxidation reduction potential of an aqueous solution, the sensor having a measurement electrode, a reference electrode, and a voltmeter to measure a voltage across the measurement electrode and the reference electrode, the method comprising:
    placing the measurement electrode and the reference electrode in the aqueous solution;
    removing at least one of the measurement electrode and the reference electrode from the aqueous solution;
    placing the at least one of the measurement electrode and the reference electrode back in the aqueous solution; and
    generating a current through the measurement electrode and the reference electrode by applying a voltage to at least one of the measurement electrode and the reference electrode for a duration of time substantially immediately after placing the at least one of the measurement electrode and the reference electrode back in the aqueous solution.

10. A method according to claim 9, wherein the aqueous solution includes a reducing aqueous solution.

11. A method according to claim 10, wherein the reducing aqueous solution is a reducing aqueous solution of a biological nutrient removal wastewater treatment process.

12. A method according to claim 11, and further comprising measuring an oxidation reduction potential of the reducing aqueous solution after the duration of time.

13. A method according to claim 9, wherein the voltage is applied when the measurement electrode and the reference electrode are at least partially submerged in the aqueous solution.

14. A method according to claim 13, and further comprising measuring an oxidation reduction potential of the aqueous solution after the duration of time.

15. A method according to claim 14, wherein the measuring an oxidation reduction potential includes measuring an oxidation reduction potential after generating a current through the measurement electrode and the reference electrode.

16. A method according to claim 14, wherein the measuring an oxidation reduction potential includes measuring an oxidation reduction potential after placing the at least one of the measurement electrode and the reference electrode back in the aqueous solution.

17. A method according to claim 16, wherein the aqueous solution includes a reducing aqueous solution.

18. A method according to claim 9, wherein the aqueous solution includes an oxidizing aqueous solution.

19. A method according to claim 9, wherein the aqueous solution includes one of an oxidizing aqueous solution and a reducing aqueous solution; and generating a current through the measurement electrode and the reference electrode includes generating a current through the measurement electrode and the reference electrode by applying a voltage having a same polarity as the aqueous solution to at least one of the measurement electrode and the reference electrode for a duration of time.

20. A method according to claim 9, wherein the aqueous solution includes a reducing aqueous solution and generating a current through the measurement electrode and the reference electrode includes generating a current through the measurement electrode and the reference electrode by applying a voltage having a negative polarity to at least one of the measurement electrode and the reference electrode for a duration of time.

21. A method according to claim 9, wherein the aqueous solution includes an oxidizing aqueous solution and generating a current through the measurement electrode and the reference electrode includes generating a current through the measurement electrode and the reference electrode by applying a voltage having a positive polarity to at least one of the measurement electrode and the reference electrode for a duration of time.

22. A method according to claim 9, wherein generating a current through the measurement electrode and the reference electrode substantially reduces the time required to achieve a representative voltage across the measurement electrode and the reference electrode after at least one of the measurement electrode and the reference electrode are at least one of exposed to air and cleaned when compared to a method of measuring an oxidation reduction potential of an aqueous solution that is the same except a current is not generated though the measurement electrode and the reference electrode.

* * * * *